United States Patent [19]
Sturrock et al.

[11] Patent Number: 5,840,848
[45] Date of Patent: Nov. 24, 1998

[54] METHOD FOR PREPARATION OF TYPE II COLLAGEN

[75] Inventors: Anna Gunilla Oberg Sturrock, Acton; Dale P. Devore, Chelmsford, both of Mass.

[73] Assignee: AutoImmune, Inc., Lexington, Mass.

[21] Appl. No.: 778,467

[22] Filed: Jan. 3, 1997

[51] Int. Cl.⁶ .............................. A61K 37/17; C07K 1/00; C07K 14/00; C07K 16/00
[52] U.S. Cl. .............................. 530/356; 514/2; 530/350
[58] Field of Search .............................. 514/2; 530/350, 530/356

[56] References Cited

U.S. PATENT DOCUMENTS

| | | |
|---|---|---|
| 3,034,852 | 5/1962 | Nishihara . |
| 3,121,049 | 2/1964 | Nishihara . |
| 3,131,130 | 4/1964 | Oneson . |
| 3,314,861 | 4/1967 | Fujii . |
| 3,530,037 | 9/1970 | Nishihara . |
| 3,949,073 | 4/1976 | Daniels et al. ............ 424/177 |
| 4,140,537 | 2/1979 | Luck et al. . |
| 4,164,559 | 8/1979 | Miyata et al. ............ 424/14 |
| 4,223,984 | 9/1980 | Miyata et al. . |
| 4,424,208 | 1/1984 | Wallace et al. . |
| 4,687,518 | 8/1987 | Miyata et al. . |
| 4,713,446 | 12/1987 | DeVore et al. . |
| 5,106,949 | 4/1992 | Kemp et al. . |
| 5,138,030 | 8/1992 | Pachenel . |
| 5,374,539 | 12/1994 | Nimni et al. . |
| 5,399,347 | 3/1995 | Trentham et al. . |
| 5,571,499 | 11/1996 | Hafler et al. . |
| 5,571,500 | 11/1996 | Hafler et al. . |

FOREIGN PATENT DOCUMENTS

| | | |
|---|---|---|
| 9404597 | 10/1995 | Brazil . |
| 898105 | 1/1960 | United Kingdom . |
| WO 88/10120 | 12/1988 | WIPO . |
| WO 91/12816 | 9/1991 | WIPO . |
| WO 91/08760 | 12/1991 | WIPO . |
| WO 92/06708 | 4/1992 | WIPO . |
| WO 94/07520 | 4/1994 | WIPO . |
| WO 97/02837 | 1/1997 | WIPO . |

OTHER PUBLICATIONS

Bayliss et al., *Biochem. J.*, 169:123–132 (1978).
Brenton et al., *Biochimie*, 68:515–525 (1981).
Cremer et al., *J. Immunol.*, 124(6):2912–2918 (1980).
Knapp et al., *Plastic and Reconst. Surg.*, 60:398–405 (1977).
Knapp et al., *J. Surg. Research*, 23:96–103 (1977).
Miller et al., *Biochem.*, 11(26):4903–4909 (1972).
Nishihara et al., *Trans. Am. Soc. Artif. Int. Organs*, 13:243–248 (1967).
Stenzel et al., *Science*, 164:1282–1283 (1969).
Steven et al., *Biochem. J.*, 135:245–247 (1973).
Trentham et al., *J. Exp. Med.*, 146:857–868 (1977).
Glade et al., *J. Bone and Mineral Reasearch*, 6:217–226, 1991.
Kirsch et al., *J. Biological Chem.*, 269:11462–11469, 1994.
McNicol et al., *Biochem. J.*, 185:705–713, 1980.
Roughley et al., *Biochem. J.*, 167:629–637, 1977.
Seyer, JM et al. Eur. J. Biochem. 181:159–173, 1989.
Etherington, DJ. Connective Tissue Res. 5:135–145, 1977.
Quteigh, D. et al. J. Biomed. Mat. Res. 24:749–760, 1990.
Rongliley, P.T et al. Biochem. J. 167:629–637, 1977.
Heinegard, D. et al. Arch. Biochem. Biophys. 165:427–441, 1974.

*Primary Examiner*—Sheela Huff
*Attorney, Agent, or Firm*—Darby & Darby

[57] ABSTRACT

An method is disclosed for removing Type I collagen-containing tissue adjoining Type II collagen-containing animal tissue comprising treatment of unprocessed Type II collagen-containing tissue in an acidic solution in the presence of an acid proteinase and subjecting the mixture to moderate agitation for a period of time sufficient to cause digestion or separation of the Type I collagen-containing tissue from the Type II collagen-containing tissue. Also disclosed are methods for removing proteoglycans from Type II collagen-containing tissue.

20 Claims, No Drawings

METHOD FOR PREPARATION OF TYPE II COLLAGEN

This application claims priority pursuant to 35 U.S.C. §119 from U.S. provisional application Ser. No. 60/009,723, filed Jan. 5, 1996, the disclosure of which is incorporated herein in its entirety.

FIELD OF INVENTION

The present invention relates to methods for processing raw Type II collagen-containing tissue to separate said tissue from adjoining Type I collagen-containing tissue (perichondrial membrane) and to further remove proteoglycans from the resulting Type II collagen-containing tissue. Both methods are employed as pretreatments in a process for producing purified Type II collagen. More particularly, the invention relates to methods wherein Type II collagen-containing tissue is treated first with one protease, such as pepsin, to facilitate removal of Type I collagen-containing tissue and then with another protease, such as trypsin, to remove proteoglycans prior to Type II collagen extraction.

BACKGROUND OF INVENTION

Collagen is the major constituent of mammalian, avian, and fish cartilage and other connective tissues. It is characterized by having a high content of glycine, proline and hydroxyproline. Structurally, all collagen molecules contain a triple-stranded, helical domain comprising the repeating amino acid sequence, Gly-X-Y, where proline is frequently found in the X-position and 4-hydroxyproline in the Y-position. The helix is composed of three polypeptides called α-chains, each about 1000 amino acids in length for the fibril-forming collagens, Types I–III, V, and XI. These chains are wound around each other to form a superhelical structure of approximately 300 nm in length and 1.5 nm in diameter (Petruska, J. A. and Hodge, A. J., *Proc. Natl. Acad. Sci., U.S.A.,* 51:871, 1964).

To date, 19 distinct collagens have been identified, each of which is encoded by a different gene (Prockop, D. J. and Kivirikko, K. I., *Ann. Rev. Biochem.,* 64:403–434, 1995). These collagens may be divided into different classes depending on their form or other structural features. Of these, the best characterized are the Type I, Type II, Type III and Type IV collagens. Types I, II, and III are the main collagen types found in connective tissues (Miller, E. J., *Collagen Types: Structure, Distribution, and Functions, In: Collagen, Volume I-Biochemistry,* Ed. M. E. Nimni, CRC Press, Boca Raton, Fla., 1988, Chapter 5, pp. 139–156). Of these three, Type I collagen is the most common. Type IV collagen is found exclusively assembled into a sheetlike meshwork in the basal laminae, of which it constitutes a major part. The preponderance of Type II collagen is found in cartilaginous structures. It is also found in the vitreous of the eye.

Extraction of Type II collagen from vertebrate tissues, (e.g. cartilage) is facilitated by removal of proteoglycans which are bound to the collagen. Proteoglycans form the "ground substance" of all connective tissues and are the substrate in which connective tissue fibers are embedded. A variety of procedures have been employed in the art for removal of proteoglycans from cartilage prior to collagen extraction, many of which use aqueous solutions of inorganic and organic salts. Purification of Type II collagen from collagen extracts generally involves differential salt precipitations to separate Type II collagen from Types I, IX, and XI collagen. Types I and II collagens coprecipitate in acidic salt precipitations and may be separated from Types IX and XI collagens. However, neutral salt precipitations are required for effective separation of Type II and Type I collagens. Purification of Type II collagen is made much easier if the Type I collagen-containing membranes are removed from the sternal (or other cartilage) source prior to extraction and purification. Such separation has been accomplished in the prior art by hand-stripping the membrane (perichondrium) from the cartilage source (Butler, W. T. and Reese, C. A., Preparation of Type II Collagen, In: *Immunochemistry of The Extracellular Matrix, Volume I. Methods,* ED. H. Furthmayr, CRC Press, Boca Raton, Fla., 1982 pp. 55–60). This is a labor-intensive process and not practical for large-scale preparation of Type II collagen. Moreover, such removal is inefficient, requiring additional processing steps to insure that Type I collagen is removed from the largely Type II collagen-containing preparation, ultimately reducing the yield of pure Type II collagen. Such processing steps include the use of sodium chloride at concentrations of about 2.5M to selectively precipitate Type I collagen from neutral pH solutions and of about 4.0M to selectively precipitate Type II collagen from neutral solutions. Large quantities of solid sodium chloride are required for these precipitations followed by additional processing steps. Residual levels of Type I collagen in the Type II collagen product may range from 0.5% to 5.0%. The present invention provides a method for highly efficient removal of the perichondrial membrane, resulting in a final preparation that will typically contain less than 1% Type I collagen.

The present inventors have discovered a method of using acid proteinases, such as pepsin, to partially digest and remove most of the perichondrium and to loosen the remainder such that gentle abrasion will result in essentially complete or complete removal of this Type I collagen membrane. Perichondrium removal reduces the number of processing steps required to purify Type II collagen, thereby simplifying the preparation of Type II collagen and reducing processing costs. Acid proteinases have routinely been used to extract collagen from tissues but have not been used to differentially separate one collagen Type from a second collagen Type. Such differential removal is particularly applicable to processes of extracting Type II collagen from cartilaginous tissues, such as sternal tissue, because the Type II collagen is "protected" by proteoglycans and is thereby not significantly digested or extracted by the enzyme during this pre-treatment.

Once the perichondrium has been removed, the cartilaginous tissue may be mechanically pulverized and treated to remove proteoglycans. Proteoglycans must be removed prior to further Type II collagen extraction. In the prior art, proteoglycans have generally been extracted using inorganic or organic salts. Solutions containing an alkali metal halide, such as sodium chloride, potassium chloride, and cesium chloride at concentrations from 1 to 5 molar (M), are capable of extracting only 15–20% of the total hexuronic acid initially present in the tissue (residual hexuronic acid, a component of proteoglycan, is used as a measure of proteoglycan extraction efficiency) (Mason, R. M. and Mayes, R. W., *Biochem. Journal,* 131:535–540, 1973). Lithium bromide (4M) and lithium chloride (6M) are more effective proteoglycan extracting agents, and can effect extraction of 70–80% of hexuronic acid from cartilage. However, lithium salts are relatively expensive and their use economically unattractive (especially in large scale operations). Furthermore, large quantities of lithium salts are required for extraction, and lithium-containing solutions must be disposed of properly to avoid an adverse environmental impact.

Aqueous solutions of Group II metal halides, such as magnesium chloride, calcium chloride, and barium chloride, have also been found useful for extracting proteoglycans from collagen-containing tissues. Extraction of cartilage with either magnesium chloride (3M) or calcium chloride (2M) results in removal of 60–70% of total hexuronic acid from bovine articular cartilage (Mason, R. M. and Mayes, R. W., *Biochemical Journal*, 131:535–540, 1973) Organic halides, such as guanidinium chloride (3–5M) and S-methylisothiouranium chloride are more efficient (80–85% removal) in extracting proteoglycans than either magnesium chloride or calcium chloride (Mason, R. M. and Mayes, R. W., *Biochemical Journal*, 131;535–540, 1973). The efficiency of proteoglycan extraction from Type II collagen-containing tissues depends on the composition of the extraction solution (i.e. halide salt) as well as on the source and age of the tissue being treated. Extraction of proteoglycans from fetal and newborn tissues is highly efficient (up to 90%) compared to extraction from adult tissues (typically only about 60%) (McNichol, D. and Roughley, P. J., *Biochemical Journal*, 185:705–713, 1980). Extraction of proteoglycans from nasal, growth, laryngeal, and tracheal cartilage (as high as 85% removal) is more efficient than from articular and knee meniscal cartilage (typically 56–62%) (Stanescu, V., et.al., *Biochim. Biophys. Acta*, 629:371–381, 1980). Extraction efficiency is also influenced by the method used: a large number of salt extractions with low salt, or a few extractions in high salt concentrations. Some additional methods for extraction of proteoglycans from tissues cited in the prior art are as follows:

Cremer et al. (*J. of Immunol.* 124:2912 (1980)) disclose removal of proteoglycans as a stage in the preparation of Type II collagen from chick sternal tissue in which the sterna are treated with a low ionic strength buffer, such as potassium phosphate buffer to remove some proteoglycans, followed by treatment with pepsin at a 5% enzyme: tissue ratio to extract collagen and subsequent chromatography steps to purify Type II collagen.

Steven and Thomas (*Biochem. J.*, 135:245 (1973)) describe a method of preparing insoluble collagen from cartilage by treating thin slices of human cartilage with a solution of hydrogen peroxide for 18 hours. The hydrogen peroxide-treated cartilage is then extensively washed with water, washed with a 1% sodium chloride solution, and subjected to digestion with trypsin at a 1% enzyme to tissue ratio. The hydrogen peroxide step was implemented to de-polymerize glycosaminoglycan side-chains of proteoglycans prior to degradation of core protein by trypsin.

Kempson, et.al.(*Biochim. Biophys. Acta*, 297:456–472, 1973), describe methods of releasing uronic acid into incubation solutions following treatment of human femoral condyles with chondroitinase and with trypsin. Trypsin is effective in releasing up to 94% of cartilage uronic acid after incubation at 37° C. for 48 hours.

Others (Heinegard and Hascall, *Arch. Biochem. Biophys.*, 165:427–442, 1974 and Roughley and Barrett, *Biochemical Journal*, 167:629–637, 1977) have shown that trypsin is effective in degrading proteoglycan extracted from cartilaginous tissues.

Trentham et al. (*J. of Exp. Med.*, 146:857 (1977)) disclose a method to prepare Type II collagen from chicken xiphoid cartilage comprising pepsin digestion at a 2% enzyme-to-tissue ratio after proteoglycan extraction using 2M magnesium chloride, centrifugation of the digest and application of the supernatant to a DEAE cellulose column followed by elution of Type II collagen with a Tris/NaCl buffer.

Bayliss et al. (*Biochem. J.*, 169:123 (1978)) disclose the extraction of proteoglycans from normal human articular cartilage by treating the cartilage with guanidinium chloride (4M) followed by separation of the cartilage proteoglycans from the collagen by CsCl density centrifugation.

The aforementioned proteoglycan extraction methods rely primarily either on mechanical disruption of cartilage by homogenization in low ionic strength solutions or on chemical extraction by concentrated solutions of salts such as magnesium chloride, calcium chloride, or guanidinium chloride. These methods do extract proteoglycans from cartilage, but they do so relatively inefficiently. Moreover, these procedures require the use of large quantities of salts followed by extensive washing of the proteoglycan-depleted cartilaginous pellet to remove residual salts, which increases the cost of such methods because of the expense involved in procuring and disposing of the large quantities of salts and the extensive processing required for these additional steps. Another disadvantage of the prior art methods is inconsistency in the purity of Type II collagen preparations made from cartilage treated with halide salts.

The present methods for removing Type I containing perichondrial membranes from Type II containing cartilage and for separating proteoglycans from Type II collagen, have been found to have surprising and unexpected advantages over the prior art methods, including but not limited to 1) consistent batch-to-batch yields and purity of Type II collagen, 2) substantially greater efficiency of extraction of proteoglycans from Type II collagen-containing tissues; and 3) an increased yield of Type II collagen from a given amount of starting material (e.g. chicken sterna).

As used herein the following terms have the meanings ascribed to them below:

$$\text{Type II Collagen Yeild} \quad \frac{\text{Amount of Type II Collagen in Product}}{\text{Amount of Type II collagen in raw material}} \times 100$$

$$\text{Type II Collagen Purity} \quad \frac{\text{Amount of collagen II in product} \times 100}{\text{Total Amount of product}}$$

$$\text{Proteoglycan removal efficiency (PRE):} \quad \frac{\text{Proteoglycan in raw material} - PG \text{ in product}}{\text{Proteoglycan contained in raw material}} \times 100$$

OBJECTS OF THE INVENTION

It is an object of the present invention to provide an efficient method for removal of Type I collagen-containing perichondrial membrane from chicken sterna. It is also an object of the present invention to provide a method for efficient removal of proteoglycans from Type II collagen-containing tissues essentially free from Type I collagen. In particular, it is an object to provide a method for proteoglycan removal from Type II collagen-containing tissue that accomplishes at least one of the following:

(a) requires small and inexpensive quantities of easily disposable extraction agents;

(b) provides for facile separation of proteoglycans from type II collagen; and (c) results in high and consistent yields of purified product.

It is yet another object of the invention to provide an improved process for obtaining, from animal tissues, Type II collagen that is substantially free from both proteoglycans and Type I collagen material.

SUMMARY OF THE INVENTION

A primary aspect of the invention is directed to an improved method for removing Type I collagen-containing tissue adjoining Type II collagen-containing animal tissue comprising treatment of unprocessed Type II collagen-containing tissue in an acidic solution in the presence of an acid proteinase, such as pepsin, and subjecting the mixture to moderate agitation for a period of time sufficient to cause digestion or separation of the Type I collagen-containing tissue from the Type II collagen-containing tissue. Nonlimiting examples of other proteolytic enzymes with activity in acidic conditions include renin (3.4.3) and acid cathepsins (B and D).

In addition, an improved method has been found for extracting and removing proteoglycans from Type II collagen-containing tissues essentially free of Type I collagen by treating comminuted tissues with a neutral proteinase followed by centrifugation to separate the soluble proteoglycans from the insoluble Type II collagen. One or more of a variety of proteases may be employed for removing proteoglycan from Type II collagen containing tissues, including trypsin (3.4.4.4) (preferred), chymotrypsin A (3.4.4.5), chymotrypsin B (3.4.4.6), pancreatopeptidase B (3.4.4.7), cathepsin C (3.4.4.9), papain (3.4.4.10), chymopapain (3.4.4.11), and ficin (3.4.4.12) (numbers in parentheses are Enzyme Commission reference numbers).

In a preferred embodiment, the invention provides a method for purifying Type II collagen from animal tissue comprising Type II collagen-containing tissue and adjacent Type I collagen-containing tissue, the method comprising first removing the Type I collagen-containing tissue, as recited above, followed by removing proteoglycans according to the method first recited above.

DETAILED DESCRIPTION OF THE INVENTION

The tissues to which the method of the present invention is preferably applied are those tissues which contain, as structural fibers, predominantly Type II collagen, such as sternal, intervertebral disc, notochord, nasal, growth, laryngeal, and tracheal cartilage from vertebrates. Because they are widely available, chicken cartilage tissues have been employed, most preferably in the form of chicken sterna, obtainable from chicken processing plants. It is preferred that the tissue be kept at 4° C. or colder prior to processing by the method of the present invention. The raw tissue is first trimmed to remove any remaining meat or bone. When using chicken sterna as the Type II collagen-containing tissue, it is preferred (and constitutes an important aspect of the invention) to remove the perichondrial membrane, which comprises largely Type I collagen, prior to any further processing of the tissue. Most cartilaginous tissues are surrounded by a fibrous perichondrial membrane. An exception appears to be articular cartilage (See R. A. Stockwell, Biology of Cartilage Cells, Cambridge University Press, Cambridge, England, 1979) and if articular cartilage is used as the source of collagen II, the step of removing Type I cartilage can be omitted. It is of course possible to remove perichondrial membranes using forceps or scalpels as taught by the prior art. Preferably, however, unprocessed meat- and bone-free sterna are placed in a dilute acid solution (e.g. acetic acid, citric acid, hydrochloric acid, and the like) (pH 2.5 to 4.0) in the presence of a proteolytic enzyme active under acid conditions, such as pepsin, and gently agitated for about 12 to 72 hours. The sterna can be stored in the acidic solution for several days, but removal of perichondrial membrane is substantially easier if pepsin is added immediately upon immersion of the sterna in the acidic solution. Acetic acid is preferred, because collagenous tissue swells in acetic acid to a larger extent than in hydrochloric acid, and this facilitates the action of the acid protease.

Generally, a dilute organic acid solution with a concentration of about 0.05M to about 1.0M is prepared and pepsin added at 100 mg/liter to 500 mg/liter. The acidic solution is preferably an acetic acid solution at a concentration of from about 0.25 to 0.75M, preferably about 0.5M. The typical concentration of pepsin in the acidic solution is from about 200 to 500 mg per liter, preferably about 300 to 400 mg per liter. Pepsin is an acidic proteinase that hydrolyzes peptides, including those with bonds adjacent to aromatic or dicarboxylic amino acid residues. For treatment of a cartilage source (such as chicken sterna) to remove adherent Type I collagen membranes, sufficient pepsin activity should be added to partially digest, soften, and loosen the Type I collagen membrane without causing digestion and extraction of significant quantities of Type II collagen from the cartilaginous tissue. The sufficiency of the pepsin activity for removing Type I membrane is determined by visual inspection of the cartilaginous tissue. Digestion, softening, and loosening of the Type I membrane should be accomplished in from about 12 to about 72 hours.

Other proteolytic enzymes with activity in acidic conditions that can be used instead of or in admixture with pepsin include: renin (3.4.4.3), and acid cathepsins (B, D). If renin, an enzyme with similar proteolytic specificity to pepsin, is used to remove Type I collagen-containing membranes, it should be used at a concentration of from about 300 to 700 mg per liter, preferably about 400 to 600 mg per liter. Cathepsin D is a carboxyendoproteinase that has been purified from bovine and rabbit spleen and demonstrates specificity similar to pepsin. Cathepsin B is a thioendoproteinase. Concentrations of capthepsins B and D required to remove perichondrial membranes are higher than those of pepsin and renin, and range from about 400 to about 1000 mg of cathepsin (either B or D) per liter. The required concentration ranges for Type I collagen-removing enzymes depends upon their activity and need to be determined for each source of the enzyme. Determinations of enzyme activity are routine for those of ordinary skill in the art.

During pepsin treatment of the Type II collagen-containing tissue, the solution can be maintained at from about 4° C. to about 28° C., but is preferably maintained at about 20° C. The tissue should be agitated during pepsin treatment, the agitation preferably comprising stirring at a rate which keeps the Type II collagen-containing tissue suspended in the acid liquid. The stirring rate depends on the volume of the mixing container and the amount of sterna added per unit volume. Loosened membranes wrap around the stir rod and are easily removed from the rod. In a typical pilot scale process, 300 chicken sterna (approximately 25 pounds) with most of the meat and bony end removed, are mixed in 60 liters of dilute organic acid containing 400 mg of pepsin per liter of solution. The sterna are dispersed in the solution using a mixing apparatus, such as a Lightnin Mixer, at about 250–350 rpm or at a speed which permits the suspension of the sterna in solution and which does not allow static settling of sterna to the bottom of the vessel.

Perichondrial membrane will typically break loose, separate from the sterna, and wrap around the stirring means, from which it can be easily removed. After treatment to remove the perichondrial membrane, the sterna are washed and rinsed with water to remove residual membrane and loosened membrane particulates. The membrane pieces are easily identified and washing should be continued until all such pieces have been washed from the intact Type II collagen-containing tissue. Occasionally, it may be necessary to wipe away loosened membrane using e.g. mechanical means or to place the Type II collagen-containing tissue in a second mixing system which incorporates some gentle abrasive motions to remove any loosened, but still adherent, perichondrial membrane not removed by water washing and rinsing.

Type II collagen-containing tissue with most to all of the perichondrium removed is then frozen to facilitate pulverization. The sterna may be cut into smaller pieces before freezing. The frozen tissue is fed into a Micron Powder Systems Mikro-Bantam Pulverizer. Liquid nitrogen is continuously passed into the grinding chamber keeping the temperature below −20° C. Sterna are pulverized into a fine powder passing through a 0.062 inch screen. This powder can be stored at about −15° C. The powdered tissue is mixed with a buffer providing a pH in the range from 7–9, preferably about pH 8. The buffer is preferably Tris buffer. The amount of powdered tissue in the slurry can range from about 1 to about 100 grams per liter, is preferably about 20 to 40 grams per liter, and is most preferably about 25 grams per liter. To the slurry is added a protease, preferably trypsin. Alternatively (or in admixtures) other neutral proteases that may be used include: chymotrypsin A, chymotrypsin B, pancreatopeptidase B, cathepsin C, papain, chymopapain, and ficin. Trypsin is solubilized in the buffer and then added to a final concentration of from about 0.005 to 0.05%, preferably from about 0.01 to 0.025%, and most preferably 0.02%. The effective concentration of trypsin depends on the specific activity of the enzyme preparation. In general, the protease to powdered tissue weight ratio should be from between about 0.05 and about 5%, and should preferably be about 0.8%. Similar enzyme to tissue weight ratios can be used when using papain, chymotrypsin, pancreatopeptidase, chymopapain, and ficin. Exact amounts will depend on the specific enzyme activity of a given lot and the source of the enzyme, and can be readily ascertained by those of ordinary skill in the art by determining the specific activity per unit weight of enzyme and then using an amount of enzymatic activity about equivalent to the trypsin activity detailed above.

After protease addition, the slurry is mixed at from about 4° C. to about 35° C., preferably at about 4° C., for about 8 to 36 hours, preferably about 15 to 20 hours, and most preferably about 17 hours. Trypsin is the preferred enzyme because it is readily available in a high purity form and is relatively inexpensive.

After mixing, the slurry is subjected to centrifugation to separate the undigested particulates from the soluble phases. The supernatant is decanted and the pellet is resuspended and washed with buffer, followed by a second centrifugation. The supernatant is again decanted, yielding a pellet that can be further digested with other enzymes and purified into a powder typically containing >99% Type II collagen. Analysis for Type I collagen impurity is done by reversed-phase HPLC according to well-known methods, and is typically less than or equal to 1%. The proteoglycan contaminant level is also typically less than or equal to 1%.

Following proteoglycan extraction, Type II-containing collagen can be further extracted and purified using methods such as those described by Trentham, 1977, except that the anionic exchange chromatography and high salt steps have been eliminated. Residual enzymes can be removed by washing and/or dialysis or diafiltration. The foregoing Type II collagen-containing product may be useful in cell culture for research purposes or in the preparation of oral pharmaceutical formulations useful in the treatment of rheumatoid arthritis as taught for example in U.S. Pat. No. 5,399,347.

All cited documents are incorporated by reference in their entirety. In case of conflict the present disclosure including its definitions will control.

The following examples are given by way of illustration only, and are not to be construed as limiting.

EXAMPLE 1

Extraction of Type II Collagen from Frozen Cryomilled Chicken Sterna

Chicken sterna were obtained from a local, USDA inspected, chicken breast de-boning plant. The sterna were kept cold or frozen until processed further. The sterna were trimmed to remove any meat or bone and then placed in a 0.5M acetic acid solution to which pepsin was then added at 400 mg per liter of solution. The sterna were suspended in the acid solution containing pepsin and agitated for greater than 2 days using a Lightnin mixer set at 280–350 rpm to remove and loosen residual meat and perichondrial membrane. The sterna were washed, drained, examined, and any remaining perichondrial membrane removed by gentle scraping. The cleaned sterna were subsequently frozen. The frozen sterna were pulverized in a Micron Powder Systems Mikro Bantam™ Pulverizer into which liquid nitrogen was fed to maintain the temperature below −20° C. The powder size was <0.062 inches. This powder may be stored frozen at −15° C. prior to processing. The powdered sterna was mixed with Tris buffer, pH 8.0, to which trypsin had been added to a concentration of 0.02%. This slurry was mixed at 4° C. for 17 hours. The proteoglycans, which were digested by trypsin, were removed by centrifuging the slurry followed by washing of the residual precipitate with 0.25 volumes of buffer, i.e., Tris buffer, pH 8.0, or deionized water followed by a second centrifugation. The resultant precipitate contained Type II collagen in an insoluble, undissolved form. This precipitate can readily be enzymatically digested to produce soluble type II collagen which can readily be purified to greater than 99% purity, at which purity it is suitable for pharmaceutical use.

EXAMPLE 2

Extraction of Type II Collagen from Frozen Cryomilled Chicken Sterna

Chicken sterna are obtained from a local, USDA inspected, chicken breast de-boning plant. The sterna are kept cold or frozen until processed further. The sterna are trimmed to remove any meat or bone and then placed in a 0.04M hydrochloric acid solution to which renin is then added at 500 mg per liter of solution. The sterna are suspended in the acid solution containing renin and agitated for greater than 2 days using a Lightnin mixer set at 280–350 rpm to remove and loosen residual meat and perichondrial membrane. The sterna are washed, drained, examined, and any remaining perichondrial membrane removed by gentle scraping. The cleaned sterna are subsequently frozen. The frozen sterna are pulverized in a Micron Powder Systems Mikro Bantam™ Pulverizer into which liquid nitrogen is fed to maintain the temperature below −20° C. The powder size is <0.062 inches. This powder may be stored frozen at −15° C. prior to processing. The powdered sterna is mixed with Tris buffer, pH 8.0, to which papain is added to a concentration of 0.04%. This slurry is mixed at 4° C. for 17 hours. The proteoglycans, which are digested by trypsin, are removed by centrifuging the slurry followed by washing of the residual precipitate with 0.25 volumes of buffer, i.e., Tris buffer, pH 8.0, or deionized water followed by a second centrifugation. The resultant precipitate contains Type II collagen in an insoluble, undissolved form. This precipitate can readily be enzymatically digested to produce soluble type II collagen which can readily be purified to greater than 99% purity, at which purity it is suitable for pharmaceutical use.

What is claimed is:

1. A method of facilitating the removal of perichondrial membrane from vertebrate cartilage tissue containing unseparated perichondrial membrane comprising contacting said cartilage with an acidic solution containing an acid protease under agitation for a period of time sufficient to digest or loosen said perichondrial membrane from said cartilage.

2. The method of claim 1 wherein the source of said cartilage is chicken sterna.

3. The method of claim 2 wherein said acid protease is pepsin.

4. The method of claim 3 wherein the concentration of said pepsin is from about 100 to about 500 mg per liter of said acidic solution.

5. The method of claim 4 wherein said acidic solution comprises 0.5M acetic acid.

6. The method of claim 5 wherein said contacting lasts for about 12 to about 72 hours.

7. The method of claim 5 wherein said contacting lasts for about 24 to about 48 hours.

8. The method of claim 6 wherein said contacting occurs at a temperature of from about 4° C. to about 37° C.

9. The method of claim 6 wherein said contacting occurs at a temperature of about 20° C.

10. A method for removing proteoglycans from Type II collagen-containing tissue essentially free from Type I collagen consisting essentially of contacting said tissue with a neutral protease-containing solution wherein said neutral protease is present at a protease to tissue weight ratio within the range of 0.05% to 5%, wherein said solution is agitated for a period of time sufficient to extract said proteoglycans from said tissue into solution; and recovering said tissue.

11. The method of claim 10 wherein said tissue is pulverized cartilage from which the perichondrial membrane has been removed prior to pulverization.

12. The method of claim 10 wherein said the source of said cartilage is chicken sterna.

13. The method of claim 11, wherein said protease is selected from the group consisting of chymotrypsin, pancreatin, papain, ficin, chymopapain, pancreatopeptidase, and trypsin, and said protease is present at a protease to tissue weight ratio of from about 0.05 to about 5%.

14. The method of claim 12, wherein said protease is trypsin, and said trypsin is present at a protease to tissue weight ratio of from about 0.05 to about 5%.

15. The method of claim 10 wherein said trypsin is present at a concentration of about 0.8%.

16. The method of claim 12 wherein said period of time is from about 8 to about 36 hours.

17. The method of claim 13 wherein said period of time is from about 15 to 20 hours.

18. The method of claim 10 wherein said contacting takes place at a temperature of about 4° C. to about 35° C.

19. The method of claim 15 wherein said contacting takes place at a temperature of about 4° C.

20. A method for obtaining Type II collagen essentially free of Type I collagen and other impurities from a meat- and bone-free collagenous tissue of vertebrate origin comprising Type II collagen, proteoglycans and a Type I collagen-containing perichondrial membrane, the method comprising:

contacting said tissue under agitation with an acidic solution containing an acid protease for a period of time sufficient to digest or loosen said membrane, and recovering said tissue essentially free of Type I collagen; and thereafter contacting said tissue under agitation with a solution at about neutral pH, said solution containing a neutral protease at a protease:tissue weight ratio within the range of 0.05%–5% for a period of time sufficient for the protease to separate proteoglycans contained in said tissue, and recovering said tissue essentially free of both Type I collagen and proteoglycans.

* * * * *

UNITED STATES PATENT AND TRADEMARK OFFICE
CERTIFICATE OF CORRECTION

PATENT NO. : 5,840,848
DATED : November 24, 1998
INVENTOR(S) : Anna Gunilla Oberg STURROCK et al.

It is certified that error appears in the above-identified patent and that said Letters Patent is hereby corrected as shown below:

On the title page, insert the following item:[60] Provisional Application

SERIAL NO. 60/009,723   JANUARY 5, 1996

Signed and Sealed this

Fifteenth Day of June, 1999

Attest:

Q. TODD DICKINSON

*Attesting Officer*          *Acting Commissioner of Patents and Trademarks*

UNITED STATES PATENT AND TRADEMARK OFFICE
CERTIFICATE OF CORRECTION

PATENT NO. : 5,840,848
DATED : November 24, 1998
INVENTOR(S) : Sturrock et al.

It is certified that error appears in the above-identified patent and that said Letters Patent is hereby corrected as shown below:

<u>Column 10,</u>
Line 4, claim 12 should read as follows:
    -- The method of claim 10 wherein said source of said cartilage is chicken sterna. --
Line 14, claim 15 should read as follows:
    -- The method of claim 14 wherin said trypsin is present at a concentration of about 0.8%. --

Signed and Sealed this

Third Day of August, 2004

JON W. DUDAS
*Acting Director of the United States Patent and Trademark Office*